(12) United States Patent
Rezzonico et al.

(10) Patent No.: US 8,467,846 B2
(45) Date of Patent: *Jun. 18, 2013

(54) MAGNETIC RESONANCE IMAGING APPARATUS AND MAGNETIC RESONANCE IMAGING METHOD

(75) Inventors: Fabio Rezzonico, Como (IT); Orfeo Contrada, Genoa (IT)

(73) Assignee: Esaote S.p.A., Milan (IT)

( * ) Notice: Subject to any disclaimer, the term of this patent is extended or adjusted under 35 U.S.C. 154(b) by 1276 days.

This patent is subject to a terminal disclaimer.

(21) Appl. No.: 11/547,667

(22) PCT Filed: Mar. 25, 2005

(86) PCT No.: PCT/EP2005/051397
§ 371 (c)(1),
(2), (4) Date: Nov. 30, 2006

(87) PCT Pub. No.: WO2005/096927
PCT Pub. Date: Oct. 20, 2005

(65) Prior Publication Data
US 2008/0045830 A1    Feb. 21, 2008

(30) Foreign Application Priority Data
Apr. 7, 2004  (IT) ............... SV2004A0015

(51) Int. Cl.
*A61B 5/05* (2006.01)
(52) U.S. Cl.
USPC ........... 600/411; 600/407; 600/415; 600/420; 324/300; 324/318; 324/322

(58) Field of Classification Search
USPC .................. 600/407, 411, 415, 420; 324/300, 324/318, 322
See application file for complete search history.

(56) References Cited

U.S. PATENT DOCUMENTS

| | | | |
|---|---|---|---|
| 4,791,371 A * | 12/1988 | Krol | 324/318 |
| 4,875,485 A | 10/1989 | Matsutani | |
| 5,197,474 A | 3/1993 | Englund et al. | |
| 5,436,607 A | 7/1995 | Chari et al. | |
| 5,689,190 A | 11/1997 | Cuppen | |

(Continued)

FOREIGN PATENT DOCUMENTS

| | | |
|---|---|---|
| EP | 0 517 452 B1 | 12/1992 |
| EP | 1 038 499 A1 | 9/2000 |

(Continued)

*Primary Examiner* — Unsu Jung
*Assistant Examiner* — Joseph M Santos
(74) *Attorney, Agent, or Firm* — Buchanan Ingersoll & Rooney PC

(57) ABSTRACT

A Magnetic Resonance imaging apparatus having a cavity in which a body or a part of a body to be imaged can be housed and a patient support device, which includes a patient supporting surface having a size so as to accommodate at least a part, particularly the whole of the patient body. The patient supporting surface is mounted in a slidable way relative to the cavity for housing the body to be imaged or a part thereof and enters together with the patient into the cavity. The patient support device includes one or more receptacles for respectively housing and/or removably coupling a coil adapted to receive signals from anatomic regions, upon excitation thereof by the Magnetic Resonance imaging apparatus. Each of the one or more receptacles are arranged over the surface of the device in areas corresponding to the position of one or more anatomic regions to be imaged.

19 Claims, 11 Drawing Sheets

U.S. PATENT DOCUMENTS

| | | | |
|---|---|---|---|
| 5,743,264 A * | 4/1998 | Bonutti | 600/415 |
| 5,779,637 A | 7/1998 | Palkovich et al. | |
| 5,808,468 A * | 9/1998 | Bis et al. | 324/318 |
| 6,045,262 A * | 4/2000 | Igeta et al. | 378/209 |
| 6,492,814 B1 | 12/2002 | Watkins et al. | |
| 6,496,007 B1 | 12/2002 | Damadian et al. | |
| 6,697,659 B1 | 2/2004 | Bonutti | |
| 6,822,447 B1 | 11/2004 | Yamagata | |
| 6,946,836 B2 * | 9/2005 | Kuhara | 324/307 |
| 7,844,318 B2 * | 11/2010 | Rezzonico et al. | 600/410 |
| 2001/0005912 A1 | 7/2001 | Duerr | |
| 2003/0062898 A1 | 4/2003 | Imai et al. | |
| 2003/0094947 A1 | 5/2003 | Akgun | |
| 2003/0204136 A1 * | 10/2003 | Green et al. | 600/415 |
| 2004/0030241 A1 | 2/2004 | Green et al. | |

FOREIGN PATENT DOCUMENTS

| | | |
|---|---|---|
| EP | 1 400 202 A1 | 3/2004 |
| EP | 1 460 443 A2 | 9/2004 |
| JP | 2000-107151 A | 4/2000 |
| WO | 03/041577 A1 | 5/2003 |

* cited by examiner

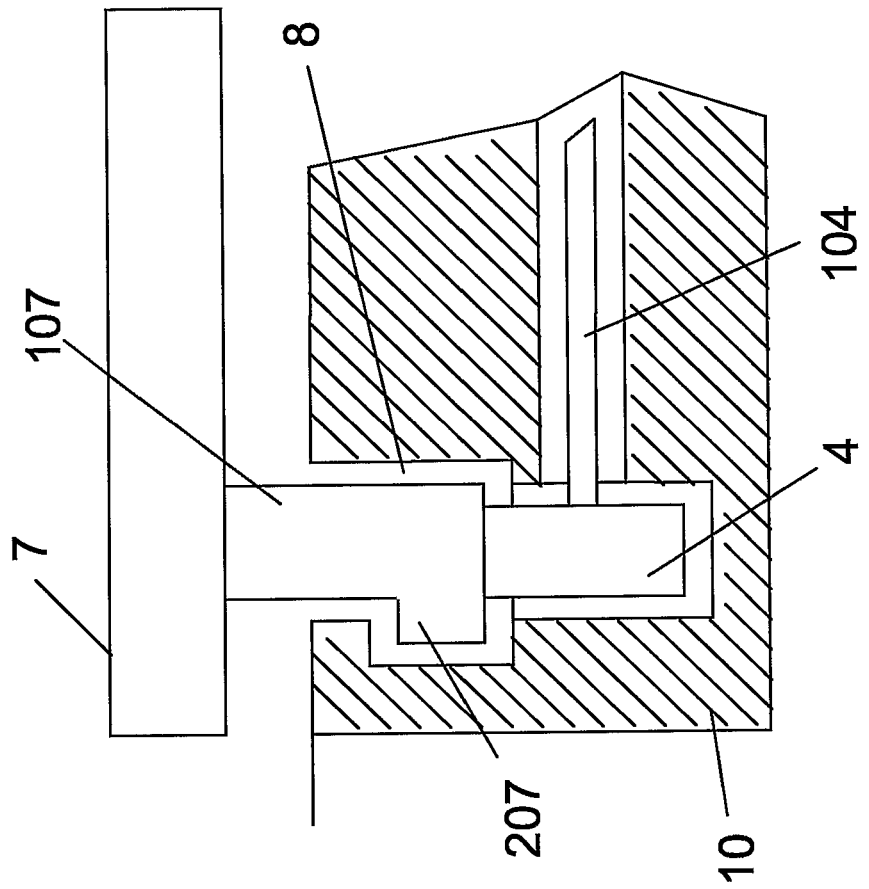
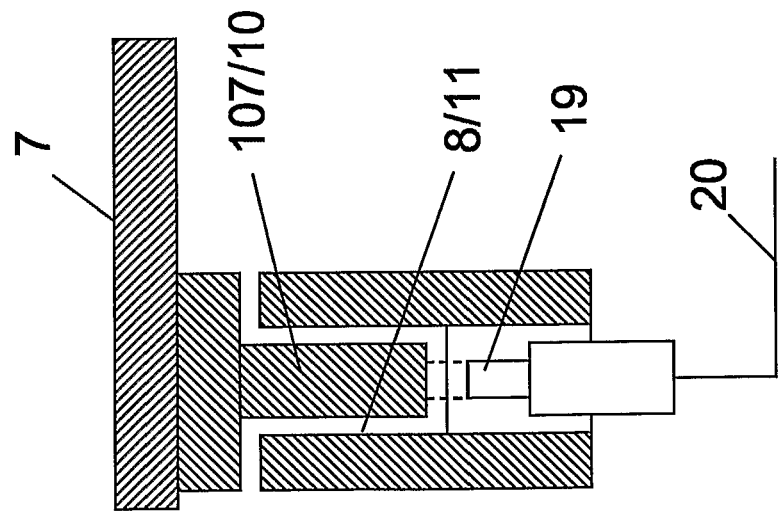
Fig. 8
Fig. 9

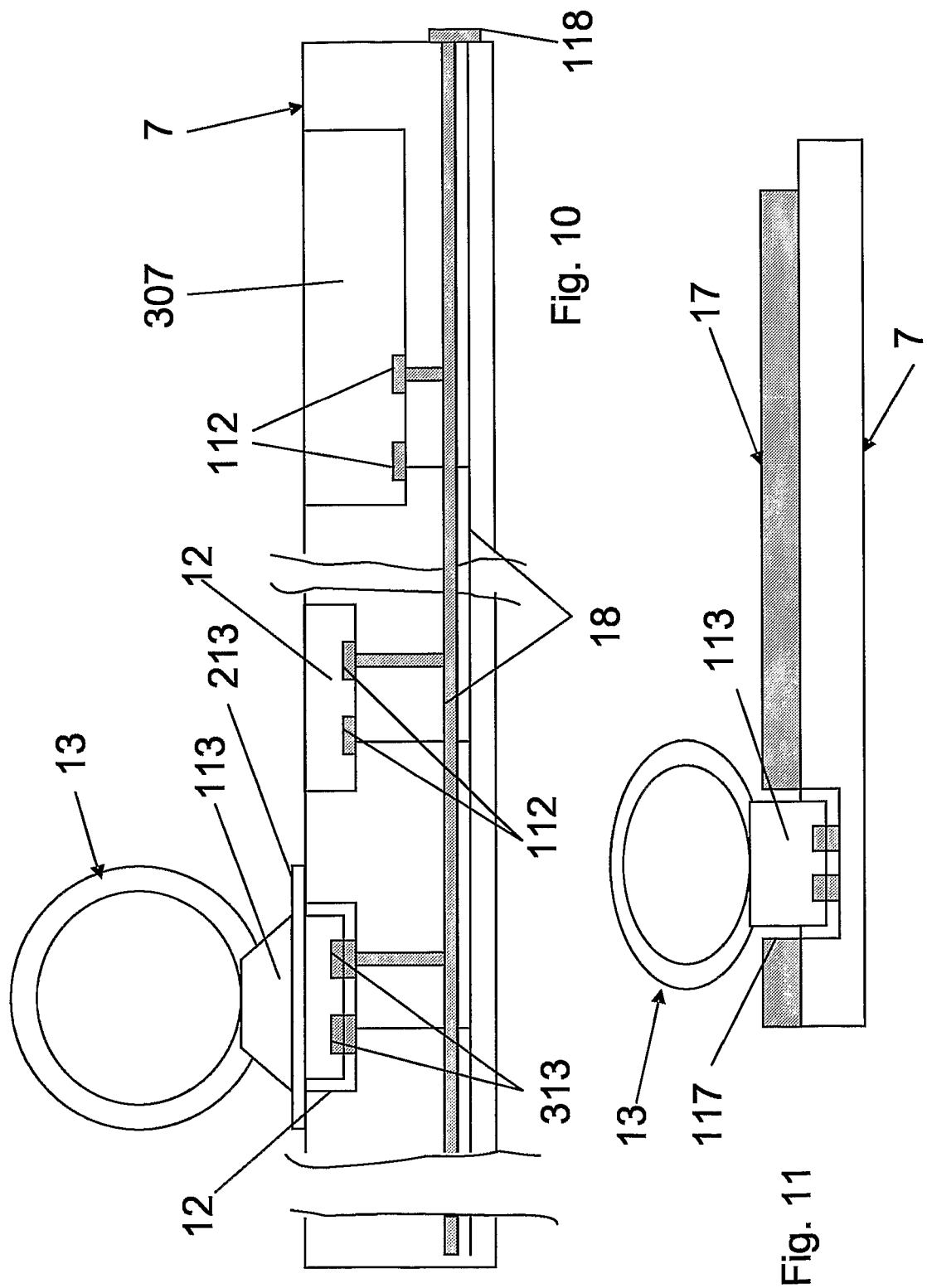

MAGNETIC RESONANCE IMAGING APPARATUS AND MAGNETIC RESONANCE IMAGING METHOD

The invention relates to Magnetic Resonance imaging apparatus having a cavity in which a body or a part of a body to be imaged can be housed and a patient support device, such as a patient bed, table or chair, comprising a patient supporting surface having such a size as to accommodate at least a part, particularly the whole of the patient body, which patient supporting means are mounted in a slidable way relatively to the cavity for housing the body to be imaged or a part thereof and enters together with the patient the said cavity.

Several different types of Magnetic Resonance imaging apparatuses are known in the art. One of these is a total body scanner apparatus, whose magnet structure can accommodate the whole patient body, or a considerable part thereof, within an imaging volume defined by the magnet structure. The patient is carried into the imaging volume by a positioning device, such as a patient bed or table mounted on a cart. Such type of apparatuses have a number of drawbacks: they have a large size, a heavy weight and a high cost and may easily cause problems during installation, i.e. they have to be installed in facilities of such a size and structural strength as to fit the size and the weight of the apparatus, which involves a further cost increase. In a second prior art arrangement an apparatus with a smaller magnet is used, and a part of the patient body is only introduced in the imaging volume, means being provided for coupling the patient support device and the magnet. However, since the receiver coil is typically secured in a fixed location within the apparatus, the patient support device requires rather complex handling, to move the anatomic region to be examined into coincidence with such receiver coil, or elements must be provided outside the patient support device, having tilting parts or the like, and in certain cases the patient must be forced to move, which is not desirable especially for patients affected with certain diseases. Eventually, this arrangement does not provide an optimal synergy between the patient support device and the Magnetic Resonance apparatus.

Therefore, the present invention has the purpose of obviating the above drawbacks and providing, by simple and inexpensive means, a patient support device as described hereinbefore, which is capable of being combined with a relatively small, light and inexpensive apparatus. Patients should be easily placed on the support device, and the positioning of the relevant anatomic region should be fast and safe, with no movement possibly having to be performed by patients, especially when several different anatomic regions have to be examined.

The invention achieves the above objects by providing a Magnetic Resonance imaging apparatus as described hereinbefore and in which the patient support device comprises at least one, two, three or more receptacles for housing and/or removably coupling a coil adapted to receive signals from anatomic regions, upon excitation thereof by the Magnetic Resonance imaging apparatus, which one, two, three or more receptacles are arranged over the surface of said device in areas corresponding to the position of one, two, three or more anatomic regions to be possibly imaged.

A receiver coil, whose shape allows it to be coupled to several anatomic regions of a body under examination may be alternately mounted in one of the housing/coupling receptacles coincident with the corresponding anatomic region to be imaged with the patient body being placed on the support table.

According to a further characteristic, the patient table according to the present invention is provided in combination with a plurality of receiver coils having such a size as to be associated to particular anatomic regions with different morphologies, said coils having engagement means complementary to the housing/coupling receptacle of the table, coincident with the relevant anatomic region of the body, with which said coil is meant to be associated.

Typically, a coil at a time is mounted on the patient table, in coincidence with an anatomic region at a time of all regions to be examined.

Nevertheless, an arrangement may be provided in which at least some or all of the receiver coils required for examination of the different anatomic regions are mounted on the patient table, when several different anatomic districts are to be examined.

In the former case, one of the different coils designed for a particular anatomic region is mounted on the table and the patient is properly positioned, or vice versa. Then, the examination is performed, whereupon said first coil is possibly replaced by a second coil designed for examination of a second different anatomic region, and so forth when examinations are to be performed in more than two different anatomic regions.

In the latter case, if possible, the coils for at least some of the anatomic regions to be examined are simultaneously mounted on the patient table, and the examinations of the different anatomic regions corresponding to the mounted receiver coils are performed one after the other, by moving said anatomic regions, as well as the corresponding coil, into the imaging volume one after the other. This is achieved, for instance, by a translational displacement of the patient table relative to the magnet structure.

Advantageously, the housing and/or coupling receptacles may have means for detecting the coil coupled to the corresponding receptacle.

The patient support device of the present invention may be provided in combination with means for displacement in at least one direction parallel and/or transverse to the longitudinal axis of the patient support surface, and in combination with a magnet structure of a Magnetic Resonance imaging apparatus, the patient table being capable of being displaced relative to said magnet structure.

According to a preferred embodiment, to be further detailed in the description of the drawings, these displacement means may allow motion of at least the patient support surface in two transverse, particularly essentially orthogonal directions, one parallel and the other transverse, particularly orthogonal to the longitudinal axis of the patient support surface.

These displacement means may be manually operable, there being provided automatic stroke limiters in one or both directions of displacement of at least the patient support surface. The limiter means may be controlled by means for detecting coils in their respective receptacles through a monitoring and controller unit which receives the signal that one or more coils are present and coupled in the corresponding housing or coupling receptacles, and, depending on the known position of the coil/s on the patient support surface, operates the displacement stroke limiting means, so that the displacement at least of the patient support surface stops at the coil/s, in a predetermined position relative to a stationary reference.

These displacement stroke limiting means may be end stop abutments whose position may be adjusted with reference to the device displacement direction/s and which are controlled on or off by the controller.

Advantageously, means may be provided for detecting the position of at least the patient support surface along one or both transverse displacement directions, which means are connected to the monitoring and controller unit.

According to a preferred embodiment, to be further detailed in the description of the drawings, the displacement means may be motor-driven and be connected to the monitoring and controller unit which, depending on the signals from the means for detecting the position of at least the patient support surface and/or depending on the signals from the means for detecting the presence of a coil in its receptacles, operates said motor driven displacement means in one or both transverse directions and during such a time or through such a stroke as to automatically move the detected coil and the associated anatomic region of the patient in a predetermined position, relative to a stationary reference.

The motor-driven displacement means may be mechanical and/or hydraulic and/or pneumatic means or combinations thereof.

The means for detecting the position of at least the patient support surface along one or both transverse displacement directions and/or relative to the stationary reference may be composed, for each motor, of at least one angular encoder, which detects the angular position of the motor shaft and communicates it to the monitoring and controller unit, which detects the displacement stroke in one or both transverse directions, therefore the position coordinates.

The means for detecting the position of at least the patient support surface may be one or more proximity sensors and/or one or more resistive sensors and/or a plurality of optical reader codes, or the like.

In combination with these motor-driven displacement means, means may be provided for stopping displacement in one or both transverse directions.

In a particular case, the motor-driven displacement means and the means for detecting the position of at least the patient support surface may be only provided for the first of the two transverse displacement directions. In this case, the displacement in the second direction may be performed manually, the displacement stopping means being only automatically operated in said second displacement direction.

The patient support device may have means for locking it in the desired displaced position in one or both transverse directions.

The patient support surface may be horizontal or essentially horizontal, or the support surface may be adjusted in its space orientation at least relative to an axis, preferably an axis transverse to the patient support surface or relative to two transverse, particularly orthogonal axes, to take any angular position.

The advantages of the present invention are self-evident from the above and consist in the capability of performing essentially the same imaging operations as a total body apparatus, while using a much smaller, lighter and less expensive apparatus. The advantages derived therefrom are an equipment as well as a facility cost reduction, much smaller size and structural strength being required from the facility than with total body apparatuses. The cost and size of a shielding Faraday cage, if any, are also considerably reduced. As regards the second prior art type of apparatus, as mentioned in the introduction, the present invention provides an optimal synergy between the patient support device and the apparatus. The patient simply takes one position on the device, as the receiver coils are not pre-mounted in the apparatus but are disposed from time to time in coincidence with the various anatomic regions, and shall not change his/her position from the initial examination position. The transverse and longitudinal stepping displacement with fixed steps corresponding to typical anatomical regions, allows to perform any examination in a very fast, safe and comfortable manner both for patients and for operators, while ensuring accurate and automatic positioning of the relevant anatomic region in coincidence with the imaging volume. Patient access is facilitated by the capability of extracting the device from the apparatus to an extreme position.

Each coil may have a base comprising an electrical output connector cooperating with an electrical input connector in a corresponding housing or coupling receptacle provided in the patient support device. The electrical output connector of the coil and the input electrical connector of the housing or coupling receptacle may be complementary and be mutually engaged and disengaged, the electrical input connectors of each receptacle being connected to the transmission line.

Advantageously, the output connectors of the coil and the input connectors of the housing or coupling receptacle may be of the press fit and release type, in the same coupling direction, particularly wherein coil bases are fitted in their respective housing and coupling receptacles on the device.

Otherwise, the electrical signal transmission line may be a common coil signal transmission line with transmission line branches connected thereto, communicating with each coil housing or coupling receptacle.

As a further alternative, the device may include a dedicated transmission line for each coil, which separately connects each coil to a coil signal processing controller in the Magnetic Resonance imaging apparatus.

The transmission line/s may be formed at least partly or wholly by shielded cables.

These transmission lines may be constructed at least partly or wholly in the form of printed circuit tracks, e.g. printed circuits boards or sheets carrying corresponding conducting tracks and fastened to the patient support surface and/or to a frame of said support surface.

The transmission line/s may terminate in an output connector which is secured to the patient support device, while a complementary connector may be provided for connecting the transmission lines associated to the device to external lines connected to the input of the processing controller of the Magnetic Resonance imaging apparatus, which may be connected to and disconnected from said output connector.

The connecting end of the output connector may be provided outside or inside the device.

The transmission line/s may be electrically and possibly also mechanically connected to the output connector by means of a connection terminal, which is capable of being coupled to and/or uncoupled from a complementary input end of the output connector.

The input connectors of the coil housing or coupling receptacles may be connected to the dedicated transmission line or to the dedicated branch of the common transmission line in a direct manner, or through complementary electrical and possibly mechanical connection terminals.

Each dedicated branch of the common transmission line may have a connection terminal that may be connected to and disconnected from one corresponding connection terminal of a plurality of connection terminals which form a plurality of inputs arranged all along the common transmission line.

All or at least some of the coil bases and the corresponding housing or coupling receptacles may be identical.

Alternatively, all or at least some of the coil bases and the corresponding housing or coupling receptacles may be different.

All or at least some of the connection terminals associated to a dedicated transmission line or to a dedicated branch of the transmission line may be identical.

Alternatively, all or at least some of the connection terminals associated to a dedicated transmission line or to a dedicated branch of the transmission line may be different.

The receptacles in which the coil bases are fastened may all have the same size, shape, mechanical fastener and electrical connection means. Otherwise, sets of receptacles may be provided in which the receptacles of each set have the same size, shape, mechanical fastener and electrical connection means, whereas the receptacles of one set may have a shape and/or a size and/or mechanical fastener means and/or electrical connection means differing from those of the receptacles of the other sets.

The Magnetic Resonance imaging apparatus, comprises usually a magnet structure which delimits a cavity for housing the patient body or at least a part thereof, and in which cavity a predetermined imaging volume is generated, wherein the relevant patient body part is to be positioned to obtain a useful image, a patient support device being associated to said magnet structure, such as a patient bed, table, chair or the like, having a patient support surface.

Said patient support surface may have at least one, two, three or more housing and/or removable coupling receptacles for at least one coil which receives signals from anatomic regions upon excitation thereof by the Magnetic Resonance Imaging apparatus, which one, two, three or more receptacles are arranged over the surface of said device in coincidence with the position of one, two, three or more different anatomic regions of the patient to be examined, and at least said patient support surface being mounted in such a manner as to be displaceable relative to the magnet structure to move one single coil, mounted in one of said housing or coupling receptacles or more of said coils, mounted in said different housing or coupling receptacles, simultaneously or successively into or into coincidence with the imaging volume. The said imaging volume is generally a limited region of the total volume of the cavity in which limited region a static magnetic filed can be generated having satisfying or sufficient homogeneity for ensuring acquisition of useful MRI images. A Further characteristics of the patient support device, combined with the inventive apparatus, have been described hereinbefore.

In a typical embodiment the magnet structure may be formed by two opposed pole pieces, which are placed at a predetermined distance from each other and extend along essentially horizontal and parallel planes. These pole pieces may be connected by an essentially vertical column or transverse wall. The pole pieces delimit a space for housing at least a part of the patient body, in which space an imaging volume is defined, which is designed to receive the anatomic region to be imaged. The patient support device may be positioned within the patient housing space, with the patient support surface extending essentially parallel to the two opposed pole pieces.

The patient support device may be displaced parallel to itself along the same plane as the patient support surface in a first direction parallel to the longitudinal direction of the patient support surface, displacement means being provided, which are supported by the magnet structure.

According to an improvement, the patient support device may be displaced in two transverse, particularly perpendicular directions, which define the patient support surface and/or a plane parallel to it and/or to least one of the pole pieces of the magnet structure.

The apparatus may comprise a controller for determining the displacement stroke of the patient support device or at least the patient support surface, which is required to move one or more coils into coincidence with the imaging volume.

The patient support device may be linked by its displacement means to one of the two pole pieces, preferably to the lower pole piece of the magnet structure.

The motor-driven displacement means may be operable for one of the two displacement directions only, whereas displacement in the other direction may be effected manually.

The present invention further relates to a Magnetic Resonance Imaging method, which provides the use of an apparatus equipped with a patient support device, particularly a patient table, the apparatus and the patient table having the above described characteristics. This method may include the steps of:

a)—positioning the patient in a lying position, essentially at the center of the patient table, the table being in an extreme displaced condition, extracted from the magnet;

b)—placing at least one receiver coil in its respective receptacle, coincident with the patient's anatomic region to be imaged;

c)—manually or automatically actuating the displacement of the patient table in at least one of the two transverse directions, to move the patient, with the coil and the associated anatomic region, into the proper position at the center of the imaging volume;

d)—locking the patient table in said position;

e)—carrying out the imaging steps;

f)—unlocking the patient table;

g)—manually or automatically displacing the patient table into an extreme position extracted from the magnet;

h)—allowing the patient to get off the table.

When the imaging procedure is to be applied to more than one anatomic region, the method may include the additional steps of:

i) once the imaging steps have been carried out by using the first coil, removing said first imaging coil and positioning a second coil in its respective receptacle, corresponding to a second patient's anatomic region to be imaged;

l)—unlocking the patient table;

m)—manually or automatically actuating the displacement of the patient table in at least one of the two transverse directions, to move the second coil and the relevant anatomic region of the patient into the proper position at the center of the imaging volume;

n)—locking the patient table in said position;

o)—carrying out the imaging steps.

Obviously, whenever further anatomic regions are to be imaged, the above detailed procedure will simply have to be repeated for each of them.

However, when possible, the invention provides an alternative method including the following steps:

p)—positioning the patient in a lying position, essentially at the center of the patient table, the table being in an extreme displaced condition, extracted from the magnet;

q)—positioning at least one set of two or more receiver coils, dedicated to one or more different corresponding anatomic regions, in its respective receptacle, coincident with the patient's anatomic region to be imaged;

r)—manually or automatically actuating the displacement of the patient table in at least one of the two transverse directions, to move the patient, with a first coil and the associated anatomic region, into the proper position at the center of the imaging volume;

s)—locking the patient table in said position;

t)—carrying out the imaging steps;

u)—unlocking the patient table;

v)—manually or automatically displacing the patient table, thereby moving the patient, with a second coil and the associated anatomic region, in the proper position, at the center of the imaging volume;

w)—locking the patient table in said position;

x)—carrying out the imaging steps;

y)—unlocking the patient table;

z)—repeating the steps v) to y) until all the anatomic regions corresponding to each of the coils of the coil set mounted on the patient table have been imaged;

aa)—after imaging the anatomic district corresponding to the last coil of the coil set mounted on the table, unlocking the patient table and moving the latter to the extreme extracted position;

bb)—allowing the patient to get off the table.

The inventive Magnetic Resonance Imaging apparatus may be further improved. The magnet structure may be supported in such a manner as to be capable of rotating about a horizontal center axis of the transverse pole piece connecting wall or column, manual or automatic means being provided for setting it into rotation. The patient table may be rigidly connected to the magnet structure, with reference to said rotation about said horizontal axis, and the magnet structure and the patient table may be rotated from a position in which the two pole pieces and the table are oriented along essentially horizontal planes to a position in which the two pole pieces and the patient table are oriented along essentially vertical planes or to a position in which the two pole pieces and the table are oriented along inclined planes between the two horizontal and vertical positions, and vice versa. Obviously, the rotation of the patient table and the magnet structure occurs when the sliding motion of the table along its longitudinal axis is locked at the corresponding pole piece.

Referring to this type of apparatus, the imaging method may further include the steps of:

cc)—after positioning the patient on the patient table, setting the magnet structure and the table into rotation from the essentially horizontal position to the essentially vertical position or to an intermediate inclined position between the two horizontal and vertical positions;

dd)—once the imaging steps have been carried out, setting the magnet structure into rotation to move the pole pieces and the patient table back to an essentially horizontal position.

Further characteristics and improvements will form the subject of the dependent claims.

The characteristics of the invention and the advantages derived therefrom will be more apparent from the following detailed description of the accompanying drawings, in which:

FIG. 8 shows an enlarged detail of FIG. 7, representing a slide and a guide and means for actuating the displacement of the patient support device.

FIG. 9 is a sectional view of the patient support device displacement stopping means.

FIG. 10 is a longitudinal sectional view of the patient support device, with a receiver coil placed in the operating position.

FIG. 11 shows a detail of FIG. 10, representing a receiver coil placed in its respective receptacle.

Figure 1:
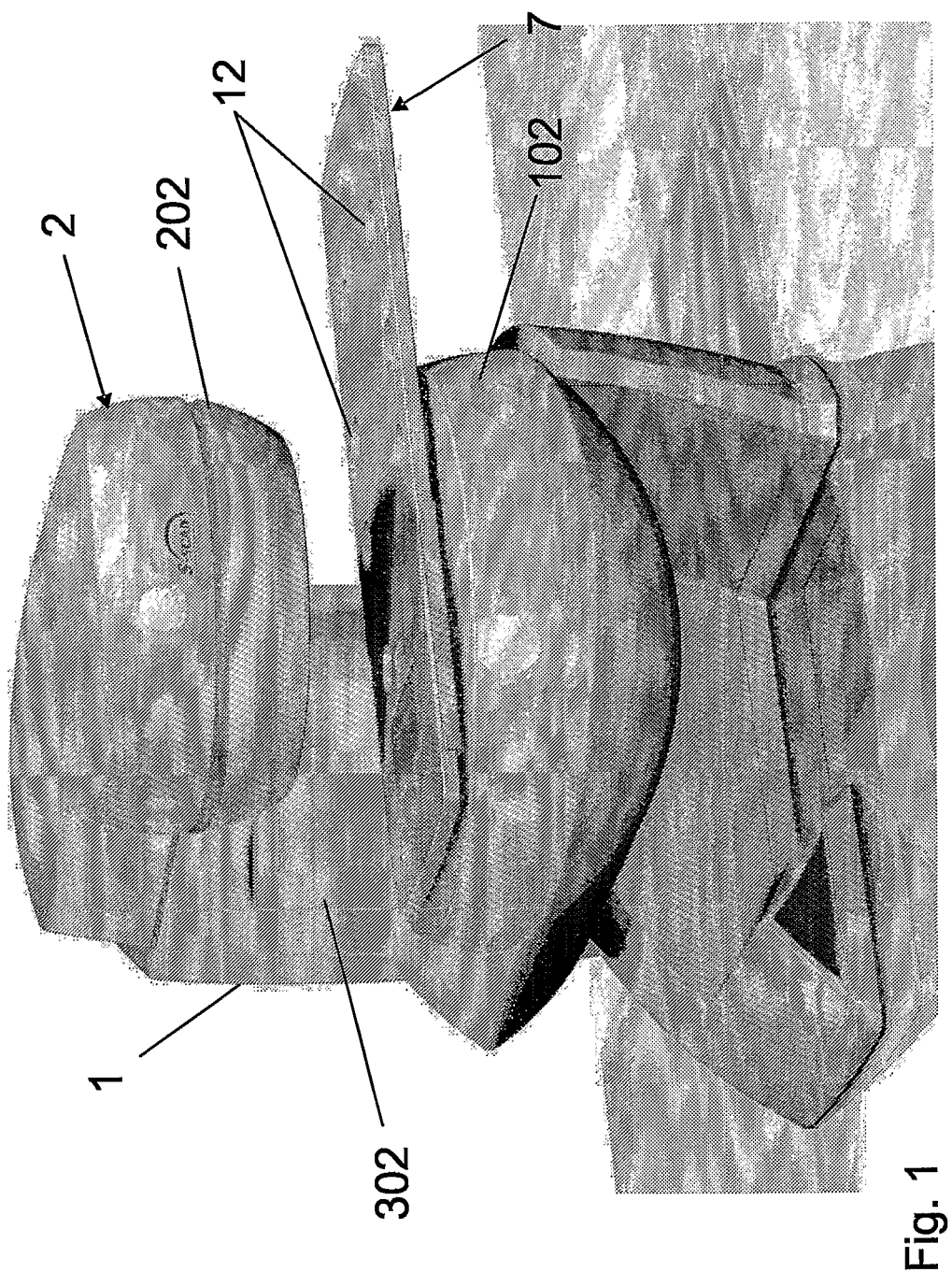
FIG. 1 is a perspective view of a preferred embodiment of a Magnetic Resonance Imaging apparatus, equipped with a patient support device according to the present invention, the pole pieces of the magnet and the device being in a horizontal position.
Figure 2:
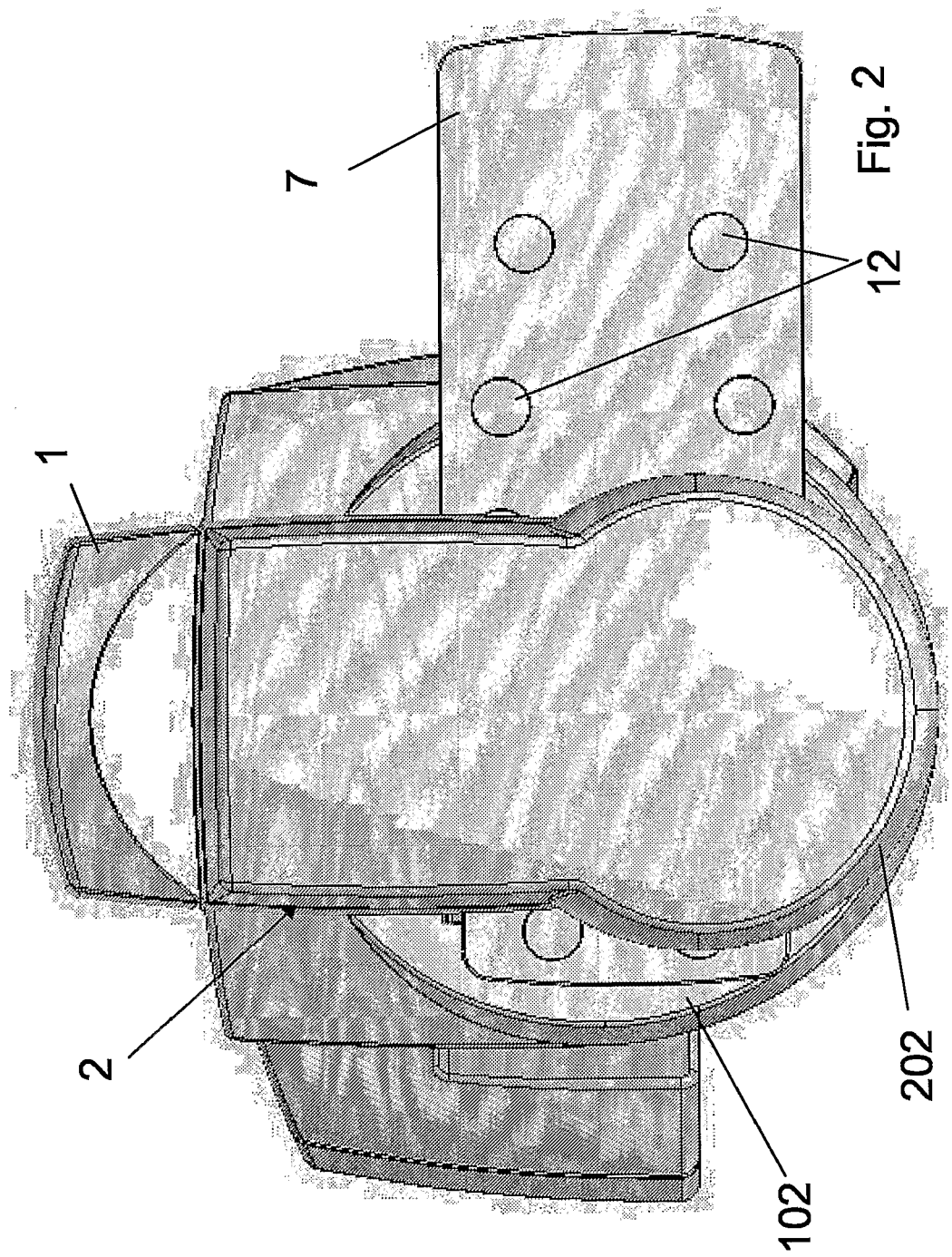
FIG. 2 is a top plan view of the apparatus and the patient support device as shown in FIG. 1.
Figure 3:
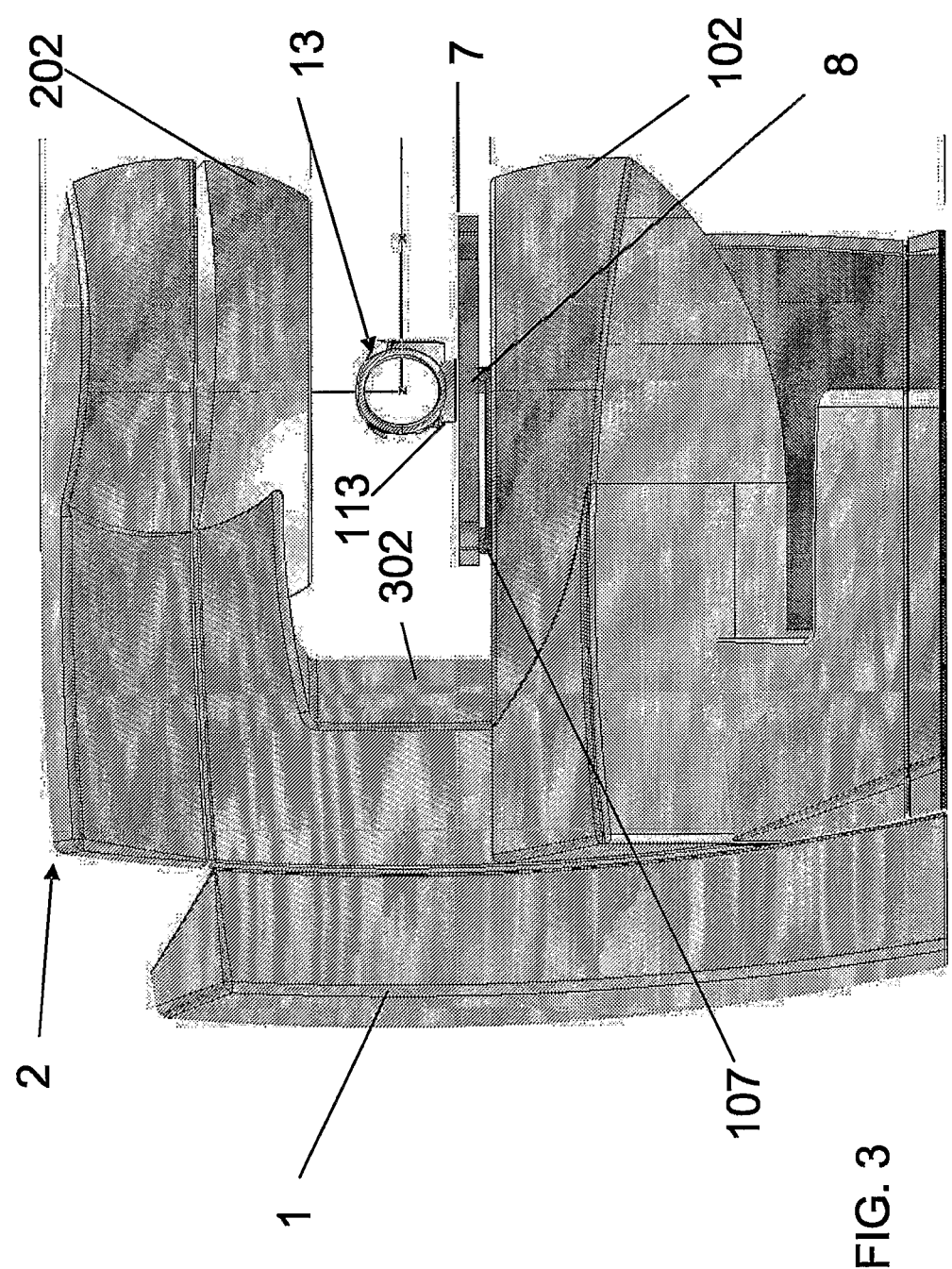
FIG. 3 is a side view of the apparatus and the patient support device as shown in FIG. 1.
Figure 4:
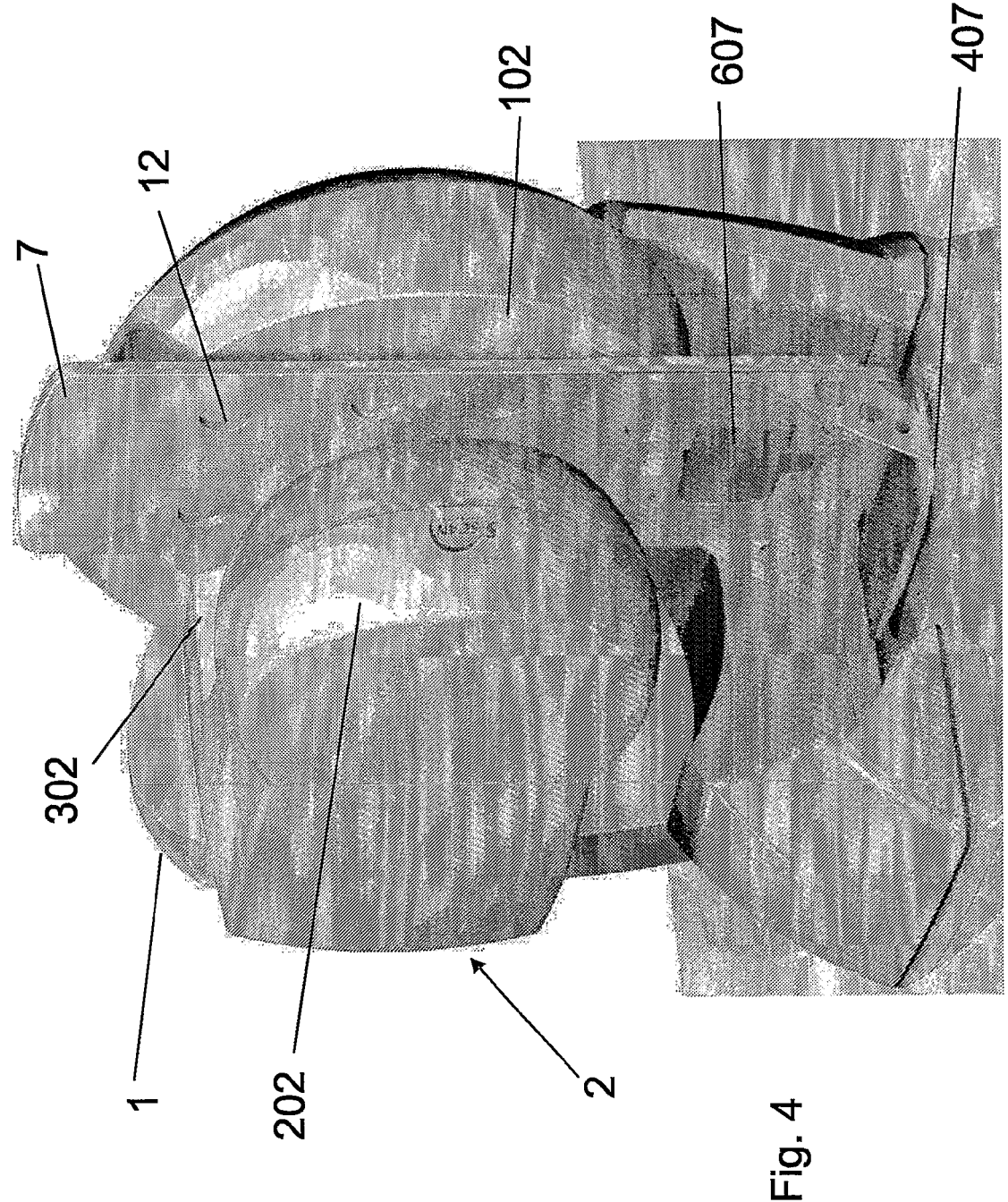
FIG. 4 is the same view as FIG. 1, with the pole pieces of the magnet and the patient support device in a vertically rotated position.

Referring to the figures, a Magnetic Resonance Imaging apparatus according to this invention first comprises a support element in the form of a vertical wall 1. A magnet structure 2 is overhangingly secured to said support element. The magnet structure 2 comprises two opposed pole pieces 102, 202, which are oriented perpendicular to the vertical support wall 1. These pole pieces 102, 202 are at a certain predetermined distance from each other and are connected by a column or wall 302 extending parallel to the vertical support wall 1, and secured to said wall 1 by means of a shaft 3, which is perpendicular to said support wall 1 and to the transverse wall 302 for connecting the pole pieces 102, 202 of the magnet structure 2. The axis of the shaft 3, which is capable of rotating within a housing in the support wall 1 is parallel to the pole pieces 102, 202 and perpendicular to the magnetic field generated therebetween. The axis of the shaft 3 coincides with the center of symmetry of the wall 302 of the magnet structure 2, although this is not required to provide the features of the apparatus. A ring gear 101 on the vertical support wall 1 cooperates with a driving pinion 4 which is driven by a motor 5 by means of a transmission 6. Thus, the motor 5 may cause the rotation of the magnet structure 2 about the axis of the shaft 3 relative to the support wall 1. It shall be noted that, although the ring gear 101 in the figures is mounted on the support wall 1, the same result might be obtained by mounting the ring gear 101 on the wall 302 of the magnet structure 2, and the motor 5, the transmission 6 and the pinion 4 on the support wall 1. This arrangement might avoid the presence of elements on the wall 302, which might hinder magnetic flux circulation within the wall 302. A patient support surface 7, essentially formed by a patient table is mounted on the lower pole piece 102 of the magnet structure 2 with its longitudinal axis perpendicular to the axis of the shaft and parallel to the wall 302 of the magnet structure 2. The support surface 7 is supported in such a manner as to be able to slide parallel to its own longitudinal axis, thanks to a combination of guides and slides, motor-driven means being provided to achieve proper positioning of the support plane 7 relative to the magnet structure 2. In this embodiment, longitudinal slides 107 are provided under the support surfaces 7 and secured thereto, which slides 107 extend along the opposed longitudinal bands of the support surface 7 and are slideably engaged in guides 8 on the transverse ends of the lower pole piece 102 of the magnet structure 2. A combination of a longitudinal rack on the bottom face of the support surface 7 and a motor-driven pinion provides a motor-driven displacement of the support surface 7 along its longitudinal axis in both directions. As shown, the racks may be also formed by one or both slides 107, whose bottom face may have a toothed surface engaging with a corresponding pinion 4' which is received in one or both guides 8. The pinion/s 4' are driven by a motor 9, through a shaft 104'. As shown particularly in FIG. 8, the slides 107 and the guides 8 have a combined undercut cross section to prevent the slides 107 from coming off the guides 8 when the magnet structure 2 and the support surface 7 are rotated together from the horizontal position to the vertical position. Many other different designs may be selected for the slides 107 and the guides 8. In a simple arrangement, a continuous tooth 207 is provided on each slide 107 for engagement with a continuous side recess on the facing side wall of the longitudinal guide 8. According with a further characteristic, the patient support surface 7 may also slide transverse to its longitudinal axis, i.e. perpendicular to the wall 302 of the magnet structure 2. This may be achieved similarly to what has been described above as regards the longitudinal displacement of the support surface 7. In the embodiment of the figures, each of the longitudinal guides 8 on each side of the lower pole piece 102 is placed on a transverse slide 10 which is engaged in a transverse guide 11. The transverse slides 10 and guides 11 may also have cross sections with mutually engaging undercuts, as described above with reference to the longitudinal guides 8 and slides 107. Transverse displacement may be actuated by a motor 9', by means of a combination of racks and pinions as described in detail with reference to the longitudinal guides 8 and slides 107. The magnet structure 2 is essentially of the dedicated type, i.e. forms an imaging volume that is shorter than the average size of adult patients. In fact, the patient support surface 7 is longer than the pole pieces 102, 202 of the magnet structure 2 and essentially as wide as the pole pieces 102, 202. The patient support surface 7 may have at one or both ends wheeled 16 support legs 15, which allow full-length extraction of the support surface 7 from the magnet structure 2, whereas the opposite end, possibly without legs may be still linked to the magnet structure 2. Furthermore, these legs 15 allow to reduce the load on the guides 8 and slides 107 when the support surface 7 is suspended in its two extreme positions. As an alternative, a frame may be provided for supporting the support surface 7, which is external and separate and may also have means for allowing the support surface 7 to slide thereon, which means may be advantageously identical to and coincident with the means 8 for sliding the patient table in the longitudinal direction, which are provided on the lower pole piece 102. Thanks to this arrangement, the support surface 7 may be separated from the magnet structure 2 and joined to the frame and vice versa. Moreover, by undocking the support surface 7 from one side of the magnet structure 2 and by docking another support surface 7 to the opposite side of the magnet structure 2 a more effective patient handling may be achieved. Thus, thanks to this arrangement, a patient may be examined while another patient is prepared for examination on a support plane 7 outside the apparatus.

Figure 5:
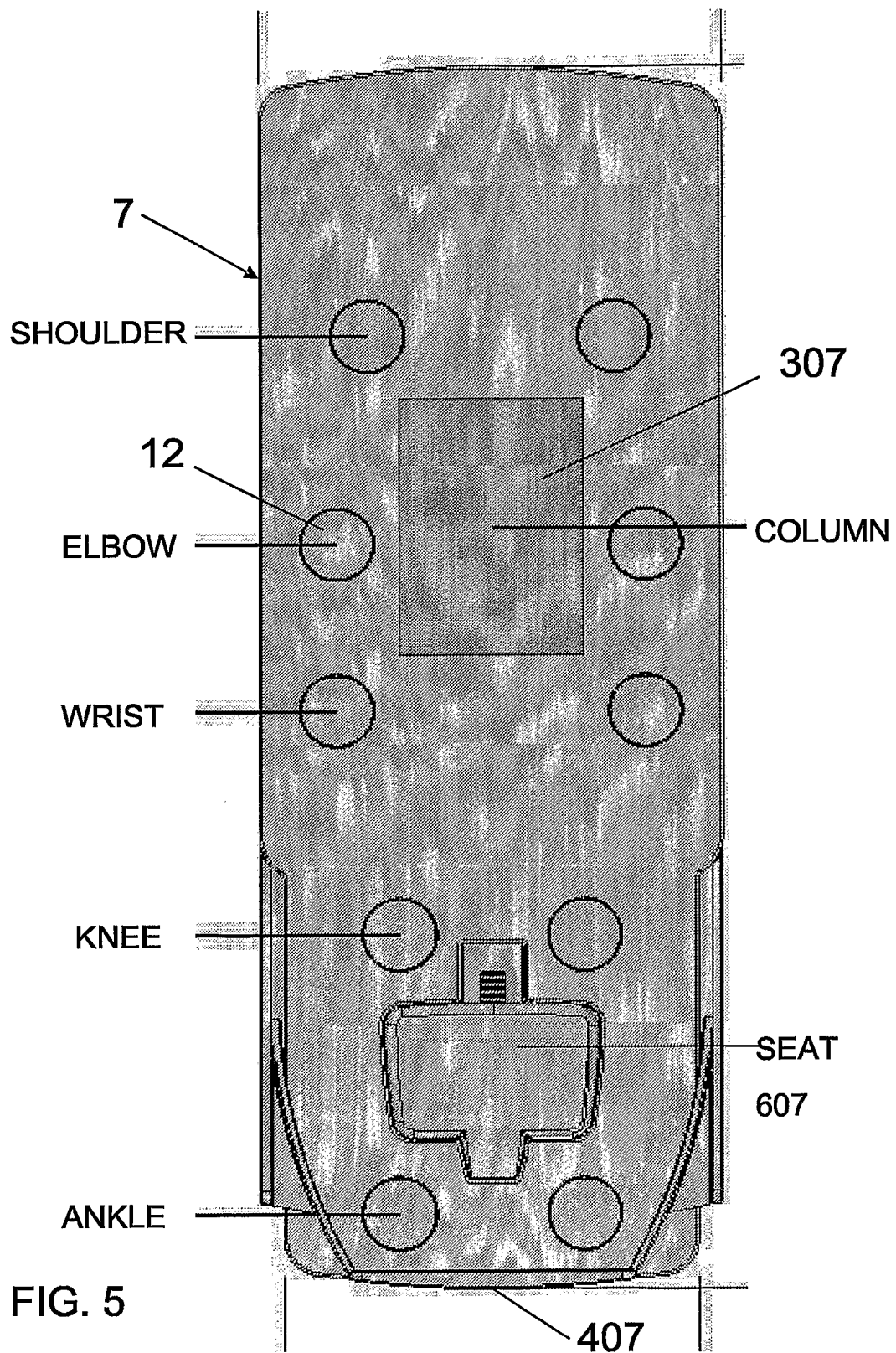
FIG. 5 is a plan view of the patient supporting side in a preferred embodiment of the patient support device according to the present invention.
Figure 6:
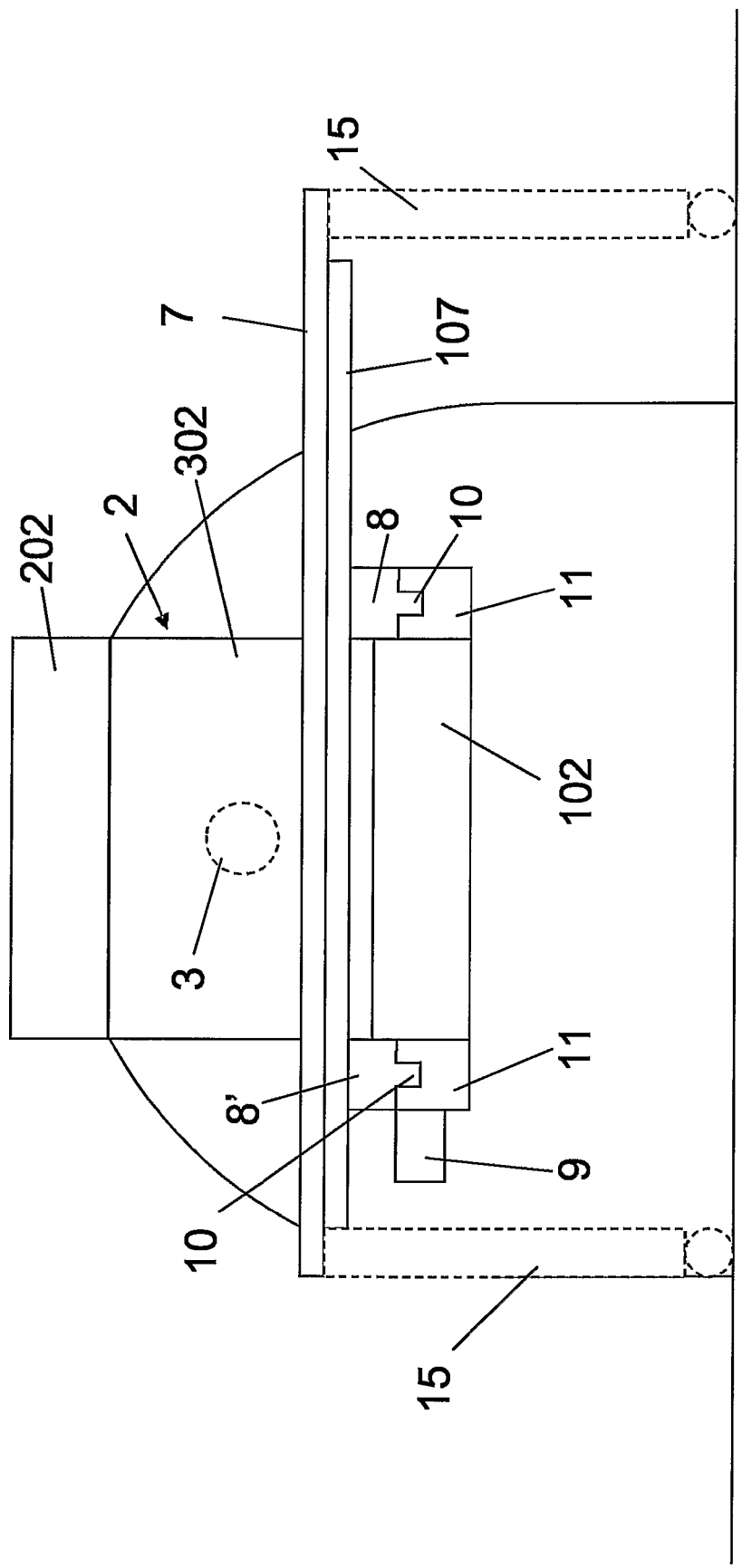
FIG. 6 is a schematic front view of the apparatus as shown in FIG. 1.
Figure 7:
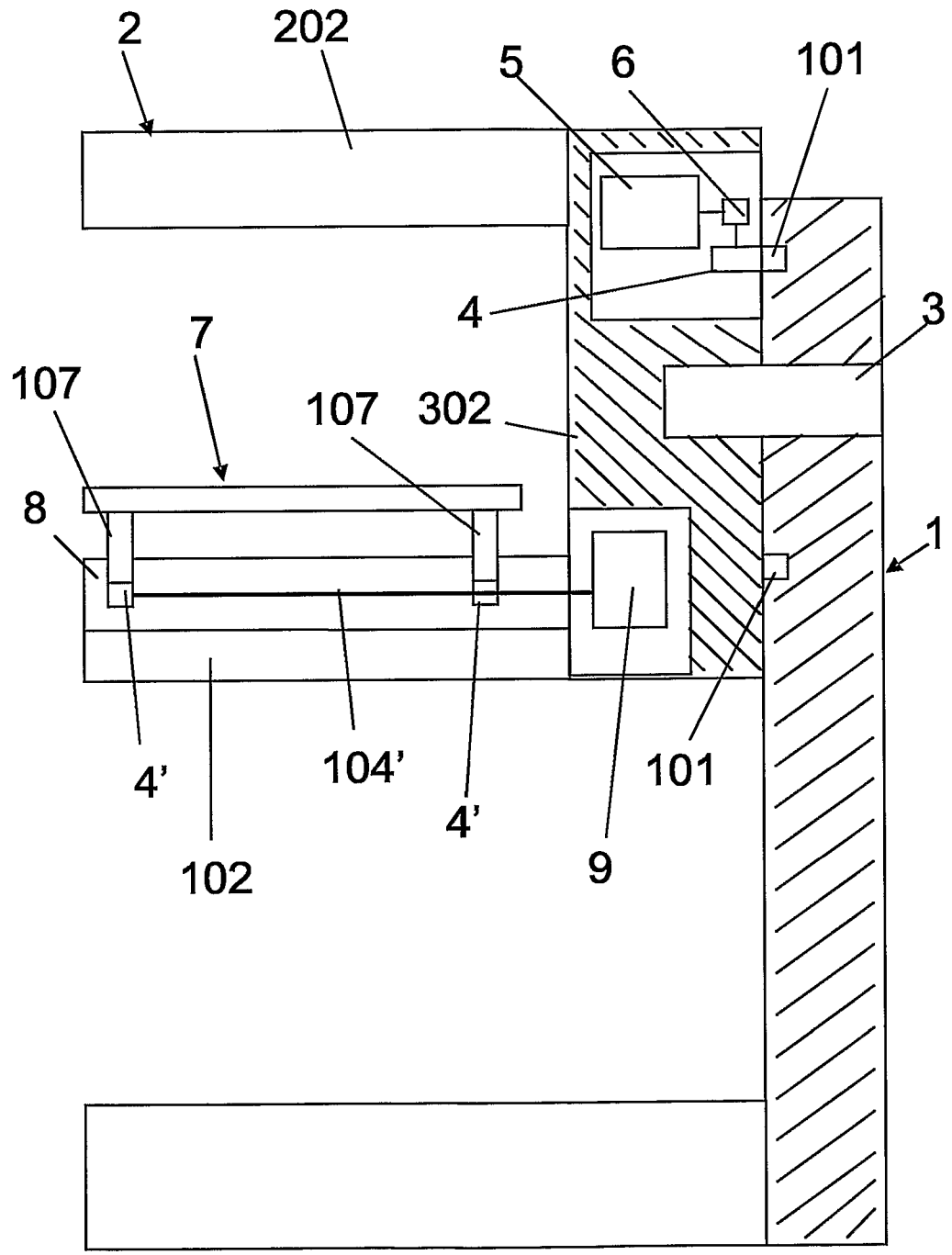
FIG. 7 is a partly sectional schematic side view of the apparatus as shown in FIG. 1.
Figure 12:
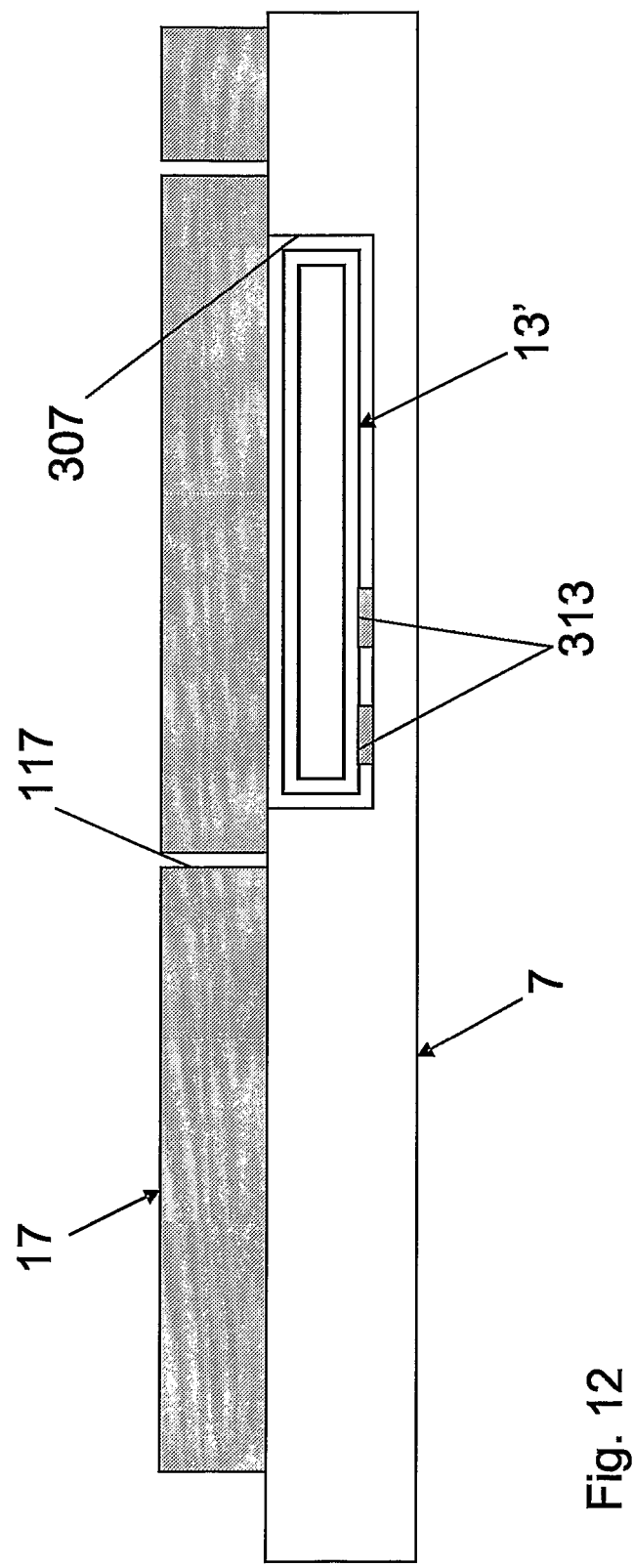
FIG. 12 is a longitudinal sectional view of the patient support device, a receiver coil being placed in the operating position for spine imaging.

Referring now to FIG. 5, a plurality of receptacles 12 each for removably locking the base 113 of a receiver coil 3 are provided on the bottom face of the lying patient support surface 7. In the embodiment of this figure, these receptacles 12 are provided in symmetric pairs, with respect to the longitudinal center axis of the support surface 7, and particularly level with the two shoulders, the two elbows, the two wrists, the two knees and the two ankles of the patient, with reference to the lying position of the patient at the center of the support plane 7. The arrangement of coils 3 resulted from an ergonomic analysis associated to the evaluation of anthropometric data, but any other arrangement that is deemed to be useful may be provided. Obviously, the coils 3 may also have different shapes, depending on the anatomic region for which they are designed. A mattress 17 is provided on the top face of the support surface 7, to increase patient comfort, and the base 113 of each coil 13 has such an axial extension as to allow introduction thereof in its locking receptacle 12 by passing through a through hole 117 formed in the mattress 17. The holes 117 that are not used during a particular examination may be closed by bearing-like closing members, which may be made from the same material as the mattress 17 or from another material. The base 113 of each coil 13 and each receptacle 12 have complementary means for removably locking the base 113 of the coil 13, which may be, for instance, a press-fit terminal provided at the lower end of the base 113 and a complementary press-fit recess provided at the bottom of the receptacle 12. An annular widened portion 213 of the base 113 of each coil 13 is further provided which, when the base 113 is fitted in its receptacle 12, abuts against the corresponding annular periphery of the receptacle 12, thereby allowing proper automatic height positioning of each coil 13 relative to the support surface 7, and allowing the coil 13 to project above the mattress 17 to the required extent. The base 113 of each coil 13 and each respective receptacle 12 have complementary electrical connectors, designated by numerals 313 and 112 respectively, which may be connected/disconnected, e.g. by automatic axial press-fit/removal, as soon as the base 113 is locked in its coupling receptacle 12 by the above mentioned mechanical means. Therefore, an operator may effect a mechanical and electrical coupling of each coil 13 essentially by axially fitting the base 113 in the receptacle 12. Each electrical connector 112 of each receptacle 12 is connected to an electrical line 18 which is designed to transmit the signal received from each coil 13 to at least one controller which processes said signal and forms the final image. Advantageously, the electric line 18 may extend within the thickness of the support surface 7 and have an electrical connector 118 for connection to another electrical connector which communicates with an external line to the controller. This arrangement allows, when required, to fully disconnect the support surface 7 from the magnet structure 2. It shall be noted that, while the figures show a single line 18 for connection of at least the coils 13 on one side, with respect to the longitudinal center axis of the patient table 7, many other electrical connection arrangements may be provided, some of which are mentioned by way of example in the above description and in the claims.

As mentioned above, the magnet structure 2 and the support surface 7 may be rotated together to move the support surface 7, the two pole pieces 102, 202 and the patient lying on the support surface 7 into an inclined or vertical position. As is known, this position is useful for performing examinations under stress of the hip, the knee and the spine, during which the part being examined is loaded with the patient's weight. In fact, in the normal condition, with the patient lying on the support surface 7, when the latter is oriented horizontally, these parts are in an unloaded, ideal condition. In this condition, many diseases may not be clearly visible, and the examination may lead to unclear or negative results, despite the fact that the patient shows the typical symptoms of a disease, for instance of the spine. To this end, a hidden housing 307 is provided on the support surface 7, coincident with the longitudinal center axis thereof, for another flat coil 13', adapted for spine examinations. This housing 307 is constructed like a drawer and may be accessed from the patient supporting side, for positioning the coil 13' therein. In the embodiment of the figures, the coil 13' has such a size that spine examinations are divided into three examinations for the cervical, thoracic and lumbar segments of the spine, although coils 13' may be used of sizes and/or types other than the ones of the figures. The size and positioning of the area required for spine examination is once more determined by anthropometric data analysis. Since the imaging method of this invention provides a rotation of the support surface 7 with the patient lying thereon, a footrest 407 is provided at the end of the support surface 7 corresponding to the patient's feet for axially holding the patient while he/she is being rotated and examined. The footrest 407 may be of the stationary type or be formed by a plate to be fixed in position on the support surface 7 after patient positioning. Otherwise, the footrest 407 may be formed by an extension of the support surface 7, which is hinged to the support surface 7 in such a manner that it can be alternately moved into and locked in an open position and an idle position, parallel to the rest of the support surface 7. In the area between the footrest 407 and the coil 13', a tilting surface 507 may be provided, having the function of a support for the knees when the legs are in the bent condition and/or the function of a chair.

As described above, means are provided for detecting the presence of a particular coil 13, 13' in its receptacle 12, 307 and for allowing the central controller to identify the coil 13, 13'. These means may be, for instance, a switch disposed in each receptacle 12, 307, which actuates a contact upon introduction of the coil 13, 13' in its receptacle 12, 307. Means are further provided for accurately determining the position of the support surface 7 relative to the imaging volume so that, when a particular coil 13, 13' is positioned on the support surface 7, the controller automatically determines the necessary movements and drives the motor 9 and/or the motor 91 and possibly the motor 5 to displace and/or rotate the support surface 7 and move it into the proper position, in which the coil 13, 131 and the anatomic region are perfectly centered with respect to the imaging volume. Nevertheless, the motor means 9, 9' and 5 may be at least partly omitted, and the displacements may be at least partly effected manually. Especially in this case, means are conveniently provided for automatically limiting the displacement in one or both transverse directions. These limiter means may be, for instance, a plurality of hydraulic bearings 19, placed in predetermined positions in the longitudinal guides 8 and/or transverse slide guides 11, which rollers 19 may be controlled by the controller from an idle position, retracted or flush with respect to the plane of the guides 8, 11, along which the associated slides 107, 10 slide, to an operating, outwardly extracted abutment position, having the function of stopping the sliding motion of the slides 107 and/or the slides 10. Each roller 19 is connected to the controller by means of a dedicated electrical connector 20. Thanks to this arrangement, the operator is not expected to make calculations to move the coil 13, 13' into the proper position, and simply has to push the patient support surface 7 in one or both transverse directions until an abutment stop position is reached. These displacement limiting devices 19 may be provided even in case of motor-driven displacement, for safety purposes. It shall be noted that, when the patient is positioned by sliding the support surface 7 relative to the magnet structure 2, the patient table 7 and the magnet structure 2 are preferably in a horizontal condition. In this condition, the patient's weight effects on the displacements are reduced to inertia and to friction, whereas gravitational effects are mostly removed. The magnet structure 2 and the support surface 7 may be rotated through an angle of less than 90°, so that body weight load on the patient's spine may be gradually adjusted. Once the imaging process has been completed, the magnet structure 2 and the support surface 7 may be rotated back to the horizontal position. Thanks to the fact that the support surface 7 is longer than the magnet structure 2, the patient may easily lie on the support surface 7, as the support surface 7 may be positioned in one of the two opposite stroke stopping positions, in which it projects out of the magnet structure 2 to a great extent. The support surface 7 may be also designed for use with other diagnostic apparatuses. The provision of a seat 507, in addition to a footrest 407, advantageously allows to perform examinations on sitting patients. Means (not shown) may be further provided for removably docking the support surface 7 to the magnet structure 2 which are especially useful during rotation. These means may be a rack and pinion combination, which may be of the type that prevents reversing if the motor is disabled. As an alternative thereto or in combination therewith, mechanical lock means may be provided, such as a removable lock tooth, engaging with the rack. These means may be brought to an operating engagement position and to an idle disengagement position by means of manual, electrical, or other types of actuators. It appears that, in addition to providing useful images of the spine, thanks to the possibility of continuously displacing the support surface 7 both in the longitudinal and in the transverse directions, different anatomic regions of the patient may be sequentially moved into the imaging space, thereby allowing to perform several examinations without asking the patient to move.

Obviously, the invention shall not be intended to be limited to the embodiment as described and illustrated herein, but may be greatly varied, especially as regards construction, without departure from the guiding principle disclosed above and claimed below.

Figure 13:
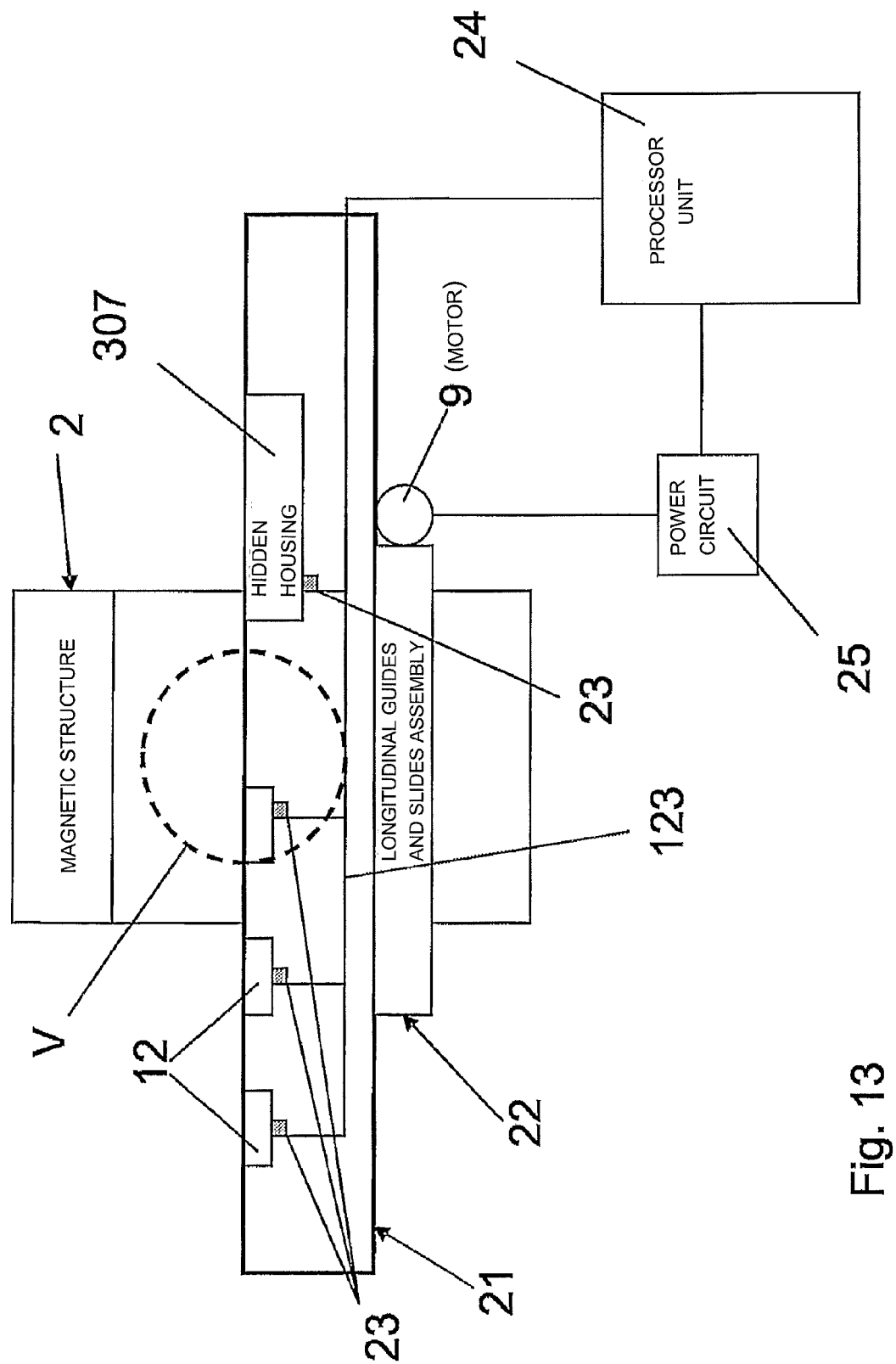
FIG. 13 shows a skeleton diagram of the system for detecting the coil and automatically positioning the patient table, relative to the magnet structure, with the detected coil within the imaging volume of the magnet structure.

Referring to FIG. 13, the patient table, designated by numeral 21 is mounted in the magnet structure 2. The assembly of all the longitudinal guides and slides is generally designated by numeral 22, whereas the longitudinally driving motor 9 is designated expressly. The patient table has several coil locking receptacles 12 and the hidden housing 307 for the receiver coil associated to the spine. A sensor for detecting the presence of each receiver coil is associated to its respective receptacle or housing, which sensor is schematically designated by the square 23. Each sensor is connected to a common communication line 123 which transmits the presence signal, uniquely corresponding to one of the receptacles 12 or to the housing 307, to a processor unit 24. The latter controls the motor 9 by means of the power circuit 25, to displace the patient table to such an extent as to move the receiver coil in one of the slots 12 into coincidence with or into the imaging volume V. The extent of displacement may be determined by the processor unit by using the known positioning coordinates of the coil or the corresponding slot 12 on the table and the previous table position or the actual table position before displacement, as detected by patient table positioning sensors, not shown in detail, which are themselves connected to the processor unit 24.

The patient table may be positioned in a direction perpendicular to the direction as shown in the figures, i.e. along an axis perpendicular to the drawing sheet, by using a method and means identical to the above description as regards longitudinal table displacement. Alternatively, the patient table may be also displaced transverse to its longitudinal axis by manual means. Here, instead of controlling a transversely driving motor, the processor unit 24 may control the actuation of end stop abutments, which are provided in such position as to limit the patient table displacement stroke transverse to the longitudinal axis of the table, said limitation being defined by the coil position on the table with reference to the transverse direction thereof, and by the displacement required to place the coil in a certain receptacle in line with the imaging volume V.

Obviously, the above is only one of the possible embodiments. The processor unit may be separate from the apparatus controlling processor unit, or a single processor unit may be provided for both functions, having suitable software, to be actuated as a patient table positioning routine.

The displacement actuators are not necessarily of the electric type, and may pneumatic, hydraulic linear actuators, or the like.

The invention claimed is:

1. A Magnetic Resonance imaging apparatus comprising:
   a cavity configured to house a patient body or a part of a patient body to be imaged; and
   a patient support device comprising:
      a patient supporting surface having a size to accommodate at least a part of the patient body, said patient supporting surface being mounted in a slidable way relative to the cavity for housing the body to be imaged or a part thereof so that the patient supporting surface enters the cavity together with the patient, and
      one or more receptacles, each receptacle housing and/or removably coupling a coil adapted to receive signals from anatomic regions of the patient, upon excitation thereof by the Magnetic Resonance imaging apparatus, wherein the one or more receptacles are arranged over the surface of said patient support device in areas corresponding to positions of one or more anatomic regions to be imaged,
      a controller for determining a displacement stroke of the patient support device or at least the patient supporting surface required to move one or more coils into coincidence with the imaging volume
   wherein the patient support device comprises:
   automatic stroke limiting means for limiting a displacement stroke of the device or at least the patient supporting surface in at least one displacement direction;
   means for detecting the presence of the coil in a selective one of said one or more housing or coupling receptacles;
   means for detecting the position of the patient support device or at least the patient supporting surface and means for detecting the stroke thereof; and
   a limit controller to control said limiting means upon reception of the signals detecting the presence of a coil in a corresponding receptacle and signals detecting the position and stroke, wherein the imaging volume provides a stationary reference to thereby align the coils with the imaging volume.

2. A Magnetic Resonance Imaging apparatus, according to claim 1, comprising a magnet structure which delimits the cavity for housing the patient body or at least a part thereof, wherein a predetermined imaging volume is defined in a region of the cavity in which a patient body part is to be positioned to obtain an image,
   wherein said patient support device is associated with said magnet structure and includes said patient supporting surface having at least one or more of the housing and/or removable coupling receptacles arranged thereon in coincidence with the positions of the one or more anatomic regions of the patient to be imaged, and
   wherein at least said patient supporting surface is mounted so as to be displaceable relative to the magnet structure to move one or more of said coils mounted in one or more of said housing or coupling receptacles, simultaneously or successively into or into coincidence with the imaging volume.

3. An apparatus according to claim 2, wherein the patient support device is displaceable in the direction of its longitudinal axis and/or in the direction of its transversal axis.

4. An apparatus as claimed in claim 2, wherein the magnet structure is formed by two opposed pole pieces arranged at a predetermined distance from each other and extending along horizontal and parallel planes, wherein the two pole pieces are connected by a transverse, vertical column or wall, and wherein the two pole pieces delimit the cavity in which the imaging volume designed to receive the anatomic region to be imaged is defined, the patient support device being positioned within the patient housing cavity, with the patient supporting surface extending parallel to the two opposed pole pieces.

5. An apparatus as claimed in claim 2, wherein the patient support device is displaceable parallel to itself along the plane of the patient supporting surface in a first direction parallel to the longitudinal direction of the patient supporting surface, the apparatus further comprising first stationary guides supported by the magnet structure, on which at least the patient supporting surface slides by means of slides.

6. An apparatus as claimed in claim 5, wherein the patient support device is displaceable in two transverse, perpendicular directions, which define the patient supporting surface and/or a plane parallel to the patient supporting surface and/or parallel to at least one of the pole pieces of the magnet structure.

7. An apparatus as claimed in claim 6, wherein the first guides slide along second guides arranged transverse and perpendicular to the first and said second guides being secured to the magnet structure.

8. An apparatus as claimed in claim 7, wherein the patient support device, or at least the patient supporting surface is linked by the guides to one of the two pole pieces of the magnet structure.

9. A Magnetic Resonance Imaging apparatus as claimed in claim 2, wherein the patient supporting surface comprises a patient table, and wherein the magnet structure is supported in such a manner as to be capable of rotating about a horizontal center axis of a transverse pole piece connecting wall or column, the apparatus further comprising:
   manual or motor means for setting the magnet structure into rotation, the patient table being rigidly connected to the magnet structure, with reference to said rotation about said horizontal axis, wherein the magnet structure and the patient table are rotatable from a position in which the two pole pieces and the table are oriented along horizontal planes to a position in which the two pole pieces and the patient table are oriented along vertical planes or are oriented along inclined planes between the horizontal and vertical positions, and vice versa, the rotation of the patient table and the magnet structure occurring when the sliding motion of the table along a longitudinal axis is locked at a corresponding pole piece.

10. A Magnetic Resonance imaging apparatus according to claim 9, wherein the patient table is disposed with its surface parallel to the magnetic field direction and/or perpendicular or transverse to the surfaces of the pole pieces which define the cavity having the imaging volume in which the patient is introduced.

11. An apparatus as claimed in claim 1, wherein the first and second guides and slides comprise displacement means for displacing the first and second guides and slides, said displacement means being manually operable.

12. An apparatus as claimed in claim 1, wherein the first and second guides and slides comprise displacement means for displacing the first and second guides and slides, said displacement means being motor-driven and provided alternatively to or in combination with the limiting means.

13. An apparatus as claimed in claim 12, wherein the motor-driven displacement means are operable for one of the two displacement directions only, and displacement in the other direction is effected manually.

14. A Magnetic Resonance Imaging method comprising:
providing the patient support device as claimed in claim 2, wherein the patient supporting surface comprises a patient table; and further comprising the steps of:
a)—positioning the patient in a lying position, at the center of the patient table, the table being in an displaced condition, extracted from the magnet structure;
b)—placing at least one receiver coil in the respective receptacle, coincident with the patient's anatomic region to be imaged;
c)—manually or automatically actuating the displacement of the patient table in at least one of two transverse directions, to move the patient, with the coil and the associated anatomic region, into a position at the center of the imaging volume;
d)—locking the patient table in said position;
e)—imaging the patient's anatomic region;
f)—unlocking the patient table;
g)—manually or automatically displacing the patient table into an position extracted from the magnet structure; and
h)—allowing the patient to get off the table.

15. A Magnetic Resonance Imaging method, as claimed in claim 14, further including the steps of:
i)—after imaging, removing the coil used for said imaging, and positioning a second coil in the respective receptacle, corresponding to a second patient's anatomic region to be imaged;
j)—unlocking the patient table;
k)—manually or automatically actuating the displacement of the patient table in at least one of the two transverse directions, to move the second coil and the associated anatomic region of the second patient, into the position at the center of the imaging volume;
l)—locking the patient table in said position; and
m)—imaging the associated anatomic region.

16. A Magnetic Resonance Imaging method, as claimed in claim 15, wherein the steps i) to m) are repeated for each further anatomic region to be imaged.

17. A Magnetic Resonance Imaging method as claimed in claim 14, the method further comprising the steps of:
positioning the patient in a lying position, at the center of the patient table, the table being in an displaced condition, extracted from the magnet structure;
placing at least one receiver coil in the respective receptacle, coincident with the patient's anatomic region to be imaged;
manually or automatically actuating the displacement of the patient table in at least one of the two transverse directions, to move the patient, with the coil and the associated anatomic region, into a position at the center of the imaging volume;
locking the patient table in said position;
setting the magnet structure and the table into rotation from the horizontal position to the vertical position or to an intermediate inclined position between the horizontal and vertical positions;
imaging the patient's anatomic region;
setting the magnet structure into rotation to move the pole pieces and the patient table back to an horizontal position;
unlocking the patient table;
manually or automatically displacing the patient table into an position extracted from the magnet structure; and
allowing the patient to get off the table.

18. A Magnetic Resonance Imaging method, as claimed in claim 17, the method further comprising the steps of:
after imaging, removing the coil used for said imaging, and positioning a second coil in the respective receptacle, corresponding to a second patient's anatomic region to be imaged;
unlocking the patient table;
manually or automatically actuating the displacement of the patient table in at least one of the two transverse directions, to move the second coil and the associated anatomic region of the second patient, into the position at the center of the imaging volume;
locking the patient table in said position; and
imaging the associated anatomic region.

19. A Magnetic Resonance Imaging method comprising:
providing the patient support device as claimed in claim 2, wherein the patient supporting surface comprises a patient table; and further comprising the steps of:
I—positioning the patient in a lying position, at the center of the patient table, the table being in an displaced condition, extracted from the magnet structure;
II—positioning at least one set of two or more receiver coils, dedicated to one or more different corresponding anatomic regions, in the respective receptacle, coincident with the patient's anatomic region to be imaged;
III—manually or automatically actuating the displacement of the patient table in at least one of two transverse directions, to move the patient, with a first coil and the associated anatomic region, into a position at the center of the imaging volume;
IV—locking the patient table in said position;
V—imaging the anatomic region;
VI—unlocking the patient table;
VII—manually or automatically displacing the patient table, thereby moving the patient, with a next coil and a next associated anatomic region, in the position, at the center of the imaging volume;
VIII—locking the patient table in said position;
IX—imaging the associated anatomic region;
X—unlocking the patient table;
XI—repeating the steps VII to X until all the anatomic regions corresponding to each of the coils of the coil set mounted on the patient table have been imaged;
XII—after imaging the anatomic region corresponding to a last coil of the coil set mounted on the table, unlocking the patient table and moving the patient table to the extracted position;
XIII—allowing the patient to get off the table.

* * * * *